(12) United States Patent
Kozaczek et al.

(10) Patent No.: US 6,678,347 B1
(45) Date of Patent: Jan. 13, 2004

(54) METHOD AND APPARATUS FOR QUANTITATIVE PHASE ANALYSIS OF TEXTURED POLYCRYSTALLINE MATERIALS

(75) Inventors: Krzysztof J. Kozaczek, State College, PA (US); David S. Kurtz, State College, PA (US); Paul R. Moran, Port Matilda, PA (US); Roger I. Martin, State College, PA (US)

(73) Assignee: HyperNex, Inc., State College, PA (US)

( * ) Notice: Subject to any disclaimer, the term of this patent is extended or adjusted under 35 U.S.C. 154(b) by 0 days.

(21) Appl. No.: 10/205,717

(22) Filed: Jul. 26, 2002

(51) Int. Cl.[7] ............................................. G01N 23/207
(52) U.S. Cl. ........................................ 378/75; 378/74
(58) Field of Search .............................. 378/69, 71, 73, 378/74, 75

(56) References Cited

U.S. PATENT DOCUMENTS

| | | | | |
|---|---|---|---|---|
| 4,592,082 | A | 5/1986 | Pawloski | 378/75 |
| 5,414,747 | A | * 5/1995 | Ruud et al. | 378/73 |
| 5,812,630 | A | 9/1998 | Blaffert | 378/83 |
| 6,108,401 | A | 8/2000 | Reefman | 378/83 |
| 6,301,330 | B1 | 10/2001 | Kurtz et al. | 378/71 |
| 2003/0012334 | A1 | * 1/2003 | Kurtz et al. | 378/73 |

OTHER PUBLICATIONS

David L. Bish et al., *Modern Powder Diffraction*, Reviews in Mineralogy, vol. 20, pp. 73–99 (The Mineralogical Society of America, 1989).

Artur March, *Mathematical Theory of the Regulation According to the Particular Shape with Affiner Deformation*, Z. Kristallographic, vol. 81, pp. 285–297 (1932).

P. Capkova and V. Valvoda, *Preferred Orientation in Powder Samples of Magnesium and Magnesium–Cadmium Alloys*, Czech J. Phys. B., vol. 24, pp. 891–900 (1974).

H.R. Wenk et al., *Texture Analysis from Diffraction Spectra*, Mat. Sci. Forum, vol. 157–162, pp. 473–480 (1994).

H.J. Bunge, Texture Analysis in Materials Science, pp. 46–118 (Butterworths, London, 1982).

P. M. de Wolf and W. H. Sas, *Instruments and Techniques Required for Accurate Relative Intensities from Powder Specimens*, Acta Cryst. A25, pp. 206–209 (1969).

V. Valvoda, *Texture Correction in Phase Analysis and Thin Film Studies*, Powder Diffraction, vol. 1, No. 2, pp. 28–32 (Jun. 1986).

B. L. Averbach and M. Cohen, *X–Ray Determination of Retained Austenite by Integrated Intensities*, Trans.AIME, vol. 176, pp. 401–415 (1948).

Ryong, Joon Roe, *Description of Crystalline Orientation in Polycrystalline Materials.: III General Solution to Pole Figure Inversion*, J. Appl. Phys., vol. 36, No. 6, pp. 2024–2031 (Jun. 1965).

Kurt Lücke et al., *On the Presentation of Orientation Distribution Functions by Model Functions*, Z. Metallkunde, vol. 77, pp. 312–321 (1986).

(List continued on next page.)

*Primary Examiner*—David V. Bruce
(74) *Attorney, Agent, or Firm*—Steven J. Hultquist; Mimi Yang; Marianne Fuierer (57) ABSTRACT

A method for quantitatively determining the phase composition of a sample mixture that comprises two or more textured polycrystalline materials, based on corrected and integrated x-ray diffraction intensities. The effect of texture has been analytically eliminated from such corrected and integrated x-ray diffraction intensities, based on the texture information obtained from the sample mixture.

21 Claims, 2 Drawing Sheets

OTHER PUBLICATIONS

K. Pawlik et al., *Rolling Texture of Silver Single Crystals Described by the Discrete Orientation Distribution*, ICOTOM 8, pp. 531–536 (ed. J.S. Kallend & G. Gottstein, The Metallurgical Society, 1988).

Daniel Ruer and Raymond Baro, *A New Method for the Determination of the Texture of Materials of Cubic Structure from Incomplete Reflection Pole Figures*, Advances in X–ray Analysis, vol. 20, pp. 187–200 (1977).

Janos Imhof, *Determination of the Orientation Distribution Function from One Pole Figure*, Textures and Microstructures, vol. 5, pp. 73–86 (1982).

S. Matthies and G.W. Vinel, *On the Reproducibility of the Orientation Distribution Function of Texture Samples from Pole Figures (Ghost Phenomena)*, Phys. Stat. Sol. (b) 92, K135–K138 (1979).

K. Pawlik, *Determination of the Orientation Distribution Function from Pole Figures in Arbitrarily Defined Cells*, Phys. Stat. Sol. (b) 134, pp. 477–483, (1986).

D. Raabe and K. Lücke, *Analysis of the ADC Method for Direct ODF Calculation by Use of Gauss Models and Standard Functions*, Materials Science Forum, vol. 157–162, pp. 413–418 (1994).

S. Matthies and G.W. Vinel, *On the Reproducibility of the Orientation Distribution Function of Texturized Samples from Reduced Pole Figures Using the Conception of a Conditional Ghost Correction*, Phys. Stat. Sol. (b) 112, K111–K114 (1982).

S. Matthies et al., Standard Distributions in Texture Analysis, vol. 1, pp. 38–45 (Akademie–Verlag, Berlin, 1987).

Bolle, B., et al., "Quantitative Phase Analysis by X–ray Diffraction of Multiphased Binary Alloy Coatings: Application to Brass Coating," J. Appl. Cryst., vol. 29 (1996) 457–464.

Bonarski, J., et al., "Improvement of Quantitative Phase Analysis of Textured Materials," Scripta Metallurgica et Materialia, vol. 25 (1991), 1401–1404.

Braun, Gerald E., "A Monte Carlo Error Simulation Applied to Calibration–Free X–ray Diffraction Phase Analysis," J. Appl. Cryst., vol. 19 (1986), 217–221.

Cheary, R.W. and Ma–Sorrell, Ying, "Quantitative Phase Analysis by X–ray Diffraction of Martensite and Austenite in Strongly Oriented Orthodontic Stainless Steel Wires," Journal of Materials Science, vol. 35 (2000) 1105–1113.

Cong, Qiu–zi, "Advances in X–ray Diffraction Based on Two–Dimensional Diffraction Theory. Derivation of the Basic Equation in Orientation Analysis," J. Appl. Cryst., vol. 27 (1994), 1042–1045.

DeBen, H.S. and Broyde, Barret, "Compositional and Texture Analysis of Tantalum Thin Films by Energy Dispersive X–ray Analysis," Applied Spectroscopy, vol. 27, No. 2 (1973), 99–102.

Dollase, W.A., "Correction of Intensities for Preferred Orientation in Powder Diffractometry: Application of the March Model," J. Appl. Cryst., vol. 19 (1986), 267–272.

Ferrari, Mauro and Lutterotti, Luca, "Method for the Simultaneous Determination of Anisotropic Residual Stresses and Texture by X–ray Diffraction," J. Appl. Phys., vol. 76, No. 11 (Dec. 1, 1994), 7246–7255.

Ferrari, M., et al., "New Opportunities in the Texture and Stress Field by the Whole Pattern Analysis," Materials Science Forum, vols. 228–231 (1996), 83–88.

Jarvinen, M., "Application of Symmetrized Harmonics Expansion to Correction of the Preferred Orientation Effect," J. Appl. Cryst., vol. 26 (1993), 525–531.

Jarvinen, M., et al., "Correction of Integrated X–ray Intensities for Preferred Orientation in Cubic Powders," J. Appl. Cryst., vol. 3 (1970), 313–318.

Li, D.Y. and O'Connor, B.H., "A Multi–line Standardless Method for X–ray Powder Diffraction Phase Analysis," Advances in X–ray Analysis, vol. 35 (1992), 105–110.

Li, D.Y. and O'Connor, B.H. "Mean–Normalised–Intensity (MNI) Method for X–ray Powder Diffraction Phase Composition Analysis," Material Science Forum, vols. 278–281 (1998) 57–62.

Lutterotti, L., et al., "Combined Texture and Structure Analysis of Deformed Limestone from Time–of–Flight Neutron Diffraction Spectra," J. Appl. Phys., vol. 81, No. 2 (Jan. 15, 1997) 594–600.

Lutterotti, L. and Scardi, P., "LS1—A Computer Program for Simultaneous Refinement of Material Structure and Microstructure," J. Appl. Cryst., vol. 25 (1992), 459–462.

Pecharskii, V.K., et al., "Method of Taking Account of Influence of Preferred Orientation (Texture) in a Powdered Specimen by Investigation of the Atomic Structure of the Substance," Sov. Phys. Crystallogr., vol. 32, No. 4 (Jul.–Aug. 1987), 514–516.

Pesonen, A., "Preferred Orientation in Tetragonal Powders," J. Appl. Cryst., vol. 12 (1979), 460–463.

Rietveld, H.M., "A Profile Refinement Method for Nuclear and Magnetic Structures," J. Appl. Cryst., vol. 2 (1969), 65–71.

Sanchez–Bajo, F., et al., "Microstructural Characterization of Y–PSZ ((4 mol%) Polycrystals by Means of X–ray Diffraction Experiments," vol. 15 (1992), 39–44.

Scardi, P., et al., "Influence of Crystallite Size and Microstrain on Structure Refinement," Materials Science Forum, vols. 79–82 (1991) 233–238.

Schmahl, W.W., et al., "An Improved Method to Determine the Weight Fraction of 2212 and 2201 Phase Impurities in BSCCO–2223 Powders from X–ray Powder Diffraction Peaks," Superconductor Science & Technology, vol. 11, No. 11 (Nov. 1998) 1269–1276.

Taut, J., et al., "Application of a New Rietveld Software for Quantitative Phase Analysis and Lattice Parameter Determination of AlN–SiC–Ceramics," Materials Science Forum, vols. 228–231 (1996), 177–182.

Valvoda, V., et al., "Joint Texture Refinement," J. Appl. Cryst., vol. 29 (1996), 48–52.

Zevin, L.S., "A Method of Quantitative Phase Analysis without Standards," J. Appl. Cryst., vol. 10 (1977), 147–150.

* cited by examiner

METHOD AND APPARATUS FOR QUANTITATIVE PHASE ANALYSIS OF TEXTURED POLYCRYSTALLINE MATERIALS

FIELD OF THE INVENTION

The present invention generally relates to the field of quantitative phase analysis, and more specifically relates to a method for determining volume and/or weight fractions of different crystalline materials in a mixture using x-ray diffraction (XRD) techniques.

BACKGROUND OF THE INVENTION

Most of the XRD-based quantitative phase analyses are based on the assumption that the measured diffraction intensity of the reflecting crystallographic planes of the sample is representative of all crystallographic planes of the same type (hkl), regardless of their orientation in the reciprocal space. However, when the sample comprises textured (i.e., having preferred crystallographic orientations) materials, the measurement result suffers from significant error, because the above-mentioned theoretical assumption is no longer true. In some cases, the error rate may be as high as 50% of the actual content of the estimated phase.

Special procedures therefore have been employed to eliminate or reduce the influence of texture on the results of XRD-based quantitative phase analysis.

For example, one may seek to mechanically eliminate texture, by grinding the sample into fine powder for preparation of a special sample. However, such approach requires complex sample preparation steps and results in complete destruction of the sample (D. L. Bish, J. E. Post, Modem Powder Diffraction, MSA, Washington, D.C., 1989, pp. 73–97).

Alternatively, one may seek to analytically eliminate texture, by using texture correction models for particles assumed to be either rod or disc shaped (A. March, Z. Kristallogr. 81, 1932, pp.285–297; W. A. Dollase, J. Appl. Cryst. 19, 1986, pp. 267–272). Those corrections apply to single component fiber textures and work relatively well for materials of weak textures. Other methods account for texture in the whole pattern refinement by describing the crystallite distribution by some analytical function (March (1932); Dollase (1986); P. Capkova, V. Valvoda, Czech J. Phys. 24, 1974, pp. 891–900).

The most advanced approach, i.e., the so-called Rietveld Texture Analysis (H. R. Wenk, S. Matthies, L. Lutterotti, Mat. Sci. Forum, Vol.157–162, 1994, pp. 473–480), uses numerous diffraction spectra collected at different sample orientations. It combines the crystallographic Rietveld refinement, the orientation distribution calculations, and some diffraction line broadening theories, and uses the least square fitting of a large number of multi-phase diffraction spectra, to obtain crystallographic texture and crystal structure information. The practical limitation of this method is that it requires collection of a very large number of diffraction spectra (often tens or hundreds for more complex materials), and takes long computation times (hours).

Experimentally, one may avoid the undesirable texture effects by selecting high multiplicity planes that produce x-ray diffraction peaks that are relatively insensitive to texture. This approach is based on experimental data obtained from careful calibration using a consistent set of samples, which is time-consuming. Moreover, this approach only works for sample materials of weak textures, and it is also vulnerable to calibration errors caused by variations of instrumental set-ups.

Another approach for eliminating texture influences from the XRD-based quantitative phase analysis involves determination of the Orientation Distribution Function (ODF) (H. J. Bunge, Texture Analysis in Materials Science, Butterworths, 1982), based on a set of experimental pole figures measured by x-ray diffraction and subsequent calculation of the pole density for each particular crystallographic reflection plane from the ODF. The calculated pole density is then used to correct the diffraction intensity measured in order to eliminate texture influences. In this approach, one pole figure is measured at a time, through a series of sample tilts with respect to the incident x-ray beam, which is time-consuming. One may also use one or more incomplete experimental pole figures and a direct method of the ODF calculation for the quantitative phase analysis, without collecting diffraction spectra in the 2Θ space (J. Bonarski, M. Wrobel, K. Pawlik, Scripta Metallurgica at Materialia, Vol. 25 (1991), pp. 1401–1404).

There are several methods that simplify the determination of the ODF, which include:

(a) making the orientation distribution cylindrically symmetrical, by spinning the sample around its normal, and then determining the symmetrical distribution from several pole distributions, wherein the ODF is described by spherical harmonic functions (P. M. de Wolf, W. H. Sas, Acta Cryst. A25, 1969, pp. 206–209; M. Jarvinen, M. Merisalo, A. Pesonen, O. Inkinen, J. Appl. Cryst. 3, 1970, pp. 313–318). However, this approach is not suitable for materials of sharp textures;

(b) measuring only the pole figures for a particular set of crystallographic planes (hkl) that are necessary for correction of the diffraction intensity $I_{textured}^{hkl}$ from the (hkl) reflection. However, this approach requires either a combination of reflection and transmission techniques, or extrapolations of incomplete pole figures that may be incorrect;

(c) for fiber textures that are common in thin films and coatings, spinning the sample around its normal, so as to eliminate the Φ variable (the azimuthal coordinate of the pole figure), and to determine the pole density $P^{hkl}(\Psi)$ for the (hkl) reflection at various Ψ angles (radial, or pole coordinate of the pole figure). This approach is experimentally simpler, but it poses the problem of open-end normalization of the pole figures (V. Valvoda, Powder Diffraction, Vol.1, No.2, 1986, pp. 28–32);

It is therefore an advantage of the present invention to provide method and apparatus for fast and accurate quantitative phase analysis of highly textured polycrystalline materials, which rapidly and automatically collects and processes x-ray diffraction data for determining volume and/or weight fractions of textured polycrystalline materials of different phases in a mixture containing the same, while avoiding the above-described disadvantages or shortcomings of the conventional approaches.

Another advantage of the present invention involves elimination of the texture-caused measurement errors from the quantitative phase analysis results, without using complex sample preparation or numerous sample measurement steps that are necessary for conventional XRD-based quantitative phase analysis methods.

Other objects and advantages will be more fully apparent from the ensuing disclosure and appended claims.

SUMMARY OF THE INVENTION

The present invention relates to a method for quantitatively determining the phase composition of a sample mixture that comprises textured polycrystalline materials of multiple phases, such method comprising the steps of:

(a) collecting multiple incomplete pole figures for the multiple phases of the sample mixture, by steps that comprise:
   (i) irradiating a measurement area on the sample mixture with radiation energy from a radiation source;
   (ii) detecting the radiation energy diffracted from the sample mixture at a detection locus, wherein the detection locus is positioned in such a way as to capture a plurality of diffraction arcs within a single data capture frame; and
   (iii) generating a diffraction image containing multiple incomplete pole figures for the multiple phases;
(b) calculating complete pole density distribution for a first set of crystallographic planes (hkl) of a first phase contained by the sample mixture, based on the incomplete pole figures collected on the diffraction image;
(c) correcting diffraction intensities collected on the diffraction image for the first set of crystallographic planes (hkl) of the first phase to eliminate crystallographic texture therefrom, by using the complete pole density distribution calculated in step (b);
(d) integrating the corrected values of diffraction intensities for the first set of crystallographic planes (hkl) of the first phase;
(e) repeating steps (b)–(d) to obtain integrated and corrected diffraction intensities for all phases contained by the sample mixture; and
(f) calculating the phase composition of the sample mixture from the corrected and integrated diffraction intensities obtained in steps (d) and (e).

In a preferred embodiment, the sample mixture comprises two textured polycrystalline materials whose crystal structures and lattice parameters are known. In an alternative embodiment, the sample mixture comprises more than two textured polycrystalline materials whose crystal structures and lattice parameters are known.

Another aspect of the present invention relates to a method for quantitatively determining phase composition of a sample mixture that comprises textured polycrystalline materials of multiple phases, said method comprising the steps of:

(a) collecting multiple incomplete pole figures for the multiple phases of the sample mixture, by steps that comprise:
   (i) irradiating a measurement area on the sample mixture with radiation energy from a radiation source;
   (ii) detecting the radiation energy diffracted from the sample mixture at a detection locus, wherein the detection locus is positioned in such a way as to capture a plurality of diffraction arcs within a single data capture frame; and
   (iv) generating a diffraction image containing multiple incomplete pole figures for the multiple phases;
(b) averaging diffraction intensities collected on the diffraction image for a first set of crystallographic planes (hkl) of a first phase over all crystallographic orientations of the incomplete pole figures collected on the diffraction image;
(c) integrating the averaged values of diffraction intensities for the first set of crystallographic planes (hkl) of the first phase in step (b);
(d) correcting the integrated diffraction intensities in step (c) with a correction factor, which is the ratio of complete pole density distribution calculated from the incomplete pole figure over incomplete pole density distribution measured for the first set of crystallographic planes (hkl) of the first phase;
(e) repeating steps (b)–(d) to obtain integrated and corrected diffraction intensities for all phases contained by the sample mixture; and
(f) calculating the phase composition of the sample mixture from the corrected and integrated diffraction intensities obtained in steps (d) and (e).

Still another aspect of the present invention relates to a quantitative phase analysis system for determining the phase composition of a sample mixture that comprises textured polycrystalline materials of multiple phases, comprising:

a sample comprising a mixture of two or more textured polycrystalline materials, defining an associated sample plane;

a radiation source for directing radiation energy to a measurement area on the sample;

a 2-dimensional area detector that registers radiation energy diffracted from the sample at the measurement area, with the radiation source and the 2-dimensional area detector being in a fixed spatial relationship to one another and sufficiently proximate to the measurement area to capture a plurality of diffraction arcs within a single data capture frame of the area detector;

a sample motion assembly for translating the sample in the sample plane; and a computer-based quantitative phase analyzer, constructed and arranged to collect and process diffraction data for determining the phase composition of the sample mixture.

Other aspects of the present invention will be more fully apparent from the ensuing disclosure and appended claims.

DETAILED DESCRIPTION OF THE INVENTION, AND PREFERRED EMBODIMENTS THEREOF

U.S. Pat. No. 6,301,330 B1 for "Apparatus and Method for Texture Analysis in Semiconductor Wafers" issued on Oct. 9, 2001 under the name of David S. Kurtz, who is a co-inventor of the present invention, is incorporated hereby by reference in its entirety for all purposes.

Generally, the integrated diffraction intensity $I_{ij}$ from a phase i contained in a mixture m that contains n phases, as measured at the j location (on one or multiple samples) is given by the following equation:

$$I_{ij} = \frac{K_i X_{ij}}{\rho_i \times \frac{\mu_m}{\rho_m}} \quad \text{with } 1 \leq i \leq n, \text{ and } 1 \leq j \leq n \tag{1}$$

Wherein $X_{ij}$ is the weight fraction of phase i in the mixture m, $\rho_i$ is the density of phase i, $\mu_m$ is the linear absorption coefficient of the mixture m, $\rho_m$ is the density of the mixture m, and $K_i$ is a constant for a given crystal structure of phase i and set of experimental conditions.

If one takes multiple measurements on one sample with varying phase composition at various locations (for example, on a mapped surface of a semiconductor wafer), or on multiple samples, a set of linear equations can be obtained, as follows:

$$\sum_{i=1}^{n} \frac{\mu_i}{\rho_i}\left(1 - \frac{I_{ij}}{I_{is}}\right) x_{is} = 0 \quad (2)$$

$$\sum_{i=1}^{n} x_{is} = 1 \text{ with } 1 \leq i \leq n, \text{ and } 1 \leq j \leq n$$

Wherein $x_{is}$ is the weight fraction of the i-th phase at location (or sample) number s, $\mu_i$ is the linear absorption coefficient of the i-th phase, $p_i$ is the density of the i-th phase, and $I_{is}$ is the integrated diffraction intensity from the i-th phase at location (or sample) number s.

The above set of equations comprises n+1 equations and n unknown variables ($x_{is}$, wherein i=1 to n), and all the n unknown variables $x_{is}$ can therefore be solved based the n+1 equations, and the phase compositions of the one sample or the multiple samples measured are thus determined.

This is usually referred to as a standardless method of quantitative phase analysis. See L. S. Zevin, J. Appl. Cryst. 10(1977) pp. 147–150.

Alternatively, the volume fraction of a phase in a sample mixture that contains multiple phases can be determined according to the direct comparison method (B. L. Averbach, M. Cohen, Trans.AIME 176, 1948, p. 401).

According to the direct comparison method, one compares diffraction intensities originating from different phases and present in one diffraction spectrum. The relation between any two of all phases present in the sample mixture is as follows:

$$\frac{I_i}{I_{i+1}} = \frac{R_i c_i}{R_{i+1} c_{i+1}} \quad (3)$$

$$\sum_{i=1}^{i=n} c_i = 1 \quad (4)$$

wherein n is the total number of phases present in the sample mixture, $I_i$ and $I_{i+1}$ are the integrated diffraction intensities from reflections of the phases i and i+1, respectively, $R_i$ and $R_{i+1}$ are the proportionality factors characteristic of the phases i and i+1, respectively, and $c_{i+1}$ and $c_{i+1}$ is the volume fractions of the phases i and i+1, respectively.

The proportionality factors $R_i$ and $R_{i-1}$ may be calculated, if the crystal structures and lattice parameters for the phases i and i+1 are known. Alternatively they may be obtained through a calibration, i.e., by using a standard with known phase composition. Another method of calibrating is to use pure-phase films of the same thickness for all phases. In such a way one would obtain the proportionality factors $R_i$ and $R_{i+1}$ experimentally for a given experimental set-up.

Another method for determining the quantitative phase composition of a sample mixture, which can be referred to as a standardless mapping method, is based on a multiple location measurement (or mapping) on a sample with variable phase composition, such as a semiconductor wafer with multiple film layers deposited on it.

The diffraction spectra from such a sample are searched in such a way as to find the spectrum containing a single phase i only. This search is conducted by matching the diffraction spectra with a spectrum corresponding to a single phase i. The ratio between the corrected diffraction intensity $I_{i0}$, as indicated on this spectrum containing the single phase i, and the corrected diffraction intensities $I_i$, as measured from other locations containing the phase i in mixture with other phases, is as follows:

$$\frac{I_i}{I_{i0}} = w_i \quad (5)$$

wherein $W_i$ is the volume fraction of the phase i contained in the mixtures at other locations, provided that the mass absorption coefficients of all phases in the mixtures are the same.

Note that other internal and external standard methods, as documented in the literature, can be used in conjunction with the above-discussed methods, for purpose of determining the quantitative phase composition from the x-ray diffraction intensities.

While the above description shows various methods for determining the phase composition of a sample mixture m containing two or more polycrystalline materials of different phases (i.e., calculating the weight or volume fractions of various phases in such mixture), based on measurement of integrated x-ray diffraction intensities, such diffraction intensity measurement has to be obtained from a perfectly random sample, wherein the measured diffraction intensity of the reflecting crystallographic planes of the sample mixture is representative if all crystallographic planes of the same type.

However, in a textured sample, the diffraction intensity actually measured is significantly reduced or increased in comparison with that measured from a perfectly random sample, due to the preferred crystallographic orientation (i.e., texture).

The relationship between the actually measured x-ray intensity $I_{textured}^{hkl}(\Psi,\Phi)$ diffracted by a set of crystallographic planes (hkl) of a textured polycrystalline material from the polar coordinates ($\Psi$, $\Phi$) in the sample coordinate system and the ideal x-ray intensity $I_{random}^{hkl}$ diffracted by planes (hkl) of a perfectly random sample is defined by:

$$I_{textured}^{hkl}(\Psi,\Phi) = I_{random}^{hkl} \times P^{hkl}(\Psi,\Phi) \quad (6)$$

wherein $P^{hkl}(\Psi,\Phi)$ is the pole density, which is the volume fraction of crystallites having the plane normal (hkl) within a solid angle element from the direction defined by the polar coordinates ($\Psi,\Phi$) in the sample coordinate system. The pole density for a perfectly random sample equals 1 for all ($\Psi,\Phi$) orientations.

Inversing equation (6), one can convert an actually measured diffraction intensity from a textured polycrystalline sample into its equivalent diffraction intensity from a perfectly random sample, if the pole density $P^{hkl}(\Psi,\Phi)$ for each $I_{textured}^{hkl}(\Psi,\Phi)$ can be determined:

$$I_{random}^{hkl} = I_{textured}^{hkl}(\Psi,\Phi) / P^{hkl}(\Psi,\Phi) \quad (7)$$

The conversion of actually measured diffraction intensity as affected by texture into an equivalent diffraction intensity as of a perfectly random sample, as disclosed in the present invention, functions to eliminate the effect of texture on the diffraction intensity measurement. It significantly enhances the accuracy of the quantitative phase analysis that is based on the diffraction intensity measurement in the present invention, and reduces the error rate of such quantitative phase analysis caused by the existence of texture in the sample material.

The pole density $P^{hkl}(\Psi,\Phi)$ of a textured polycrystalline material can be calculated from the Orientation Distribution Function (ODF), which is the quantitative measure of texture, as disclosed by U.S. Pat. No. 6,301,330 B 1.

Specifically, U.S. Pat. No. 6,301,330 B1 discloses a method that uses an area x-ray detector, a unique set of sample motions, a particular fixed special geometrical relationship between the x-ray beam source, the area x-ray detector, and the sample measurement point, and a unique and innovative texture analysis protocol for capturing multiple incomplete pole figures within one data capture frame and calculating the ODF from such incomplete pole figures, via pole figure inversion.

The use of area x-ray detector, as opposed to the point scanning detectors traditionally used for detecting diffracted x-ray beams, greatly reduces data acquisition time by capturing x-ray diffraction with a relatively large range in the $2\theta$ direction and $\Psi$ direction. Multiple diffraction arcs (i.e., sections of Debye rings) can thus be captured within a single detector frame, so as to reduce data acquisition time and increase accuracy.

The x-ray beam source and the area x-ray detector are also arranged in carefully-chosen fixed spatial relationship (thus fixed ranges of $2\theta$ and $\Psi$) that are optimally integrated with the particular set of sample motions used (only within the sample plane as defined by the planar surface of the sample), which enables the elimination of the Eulerian cradle and the $\theta$-$2\theta$ rotating stages used in the traditional x-ray diffraction system.

U.S. Pat. No. 6,301,330 B1 also provides a texture analysis protocol that simultaneously analyzes the diffraction information from all the diffraction arcs captured within the detector area, which enables fine meshing of the $\Phi$ and $\Psi$ angles, and determination of the ODF value from incomplete pole figures.

The three-dimensional distributions of crystal orientation (i.e., ODF) in polycrystalline aggregates can be calculated from two-dimensional projections of ODF (i.e., pole figures), by means of direct pole figure inversion or by series expansion methods. The series expansion methods {(H. J. Bunge, Texture Analysis in Materials Science (Butterworths, London, 1982)), (R. J. Roe, "Description of crystalline orientation in polycrystalline materials. (II) General solution to pole figure inversion," J. Appl. Phys. 36 (1965), 2024–2031)}, and the series expansion method using Gauss-type model functions (K. Lucke, J. Pospiech, and J. Jura, Z. Metallkunde 77 (1986), 312) has intrinsic truncation errors and are not suited for analyzing sharp textures (W. Truszkowski, J. Pospiech, T. Pawlik, "Rolling Texture of Silver Single Crystals Described by the Descrek Orientation Distribution, ICOTOM 8, ed. J. S. Kallend & G. Gottstein, TMS, P 531–536, 1988). The direct methods, including the vector method (D. Ruer and R. Barro, Adv. X-ray Anal. 20 (1977), 187), the Imhof method (J. Imhof, Textures and microstructures, 4 (1982), 189), the Williams-Imhof-Matthies-Vinel (WIMV) method (S. Matthies, "On the reproducibility of the orientation distribution function of texture samples from pole figures (ghost phenomena), Phys. Stat. Sol. (b) 92 (1979), K135–K138), and the Arbitrary Defined Cell (ADC) method (K. Pawlik, Phys. Stat. Sol. (b) 124 (1986), 477) may lead to errors caused by the under-determination of the set of linear equations relating discrete cells in pole figures to cells in the three-dimensional orientation space. In the case of sharp textures, the WIMV method and the ADC method work the best (D. Raabe and K. Lucke, "Analysis of the ADC Method for Direct ODF Calculation by Use of Gauss Models and Standard Functions," Materials Science Forum 157–162 (1994) 413–418).

The ODF calculation protocols of U.S. Pat. No. 6,301,330 B1 therefore utilize a direct method with an arbitrary step resolution (e.g., 1, 2, 3, and 5 degrees). The direct method is either a modified WIMV method (S. Matthis and G. W. Vinel "On the reproduction of the orientation distribution function of textured samples from reduced pole figures using conceptions of a conditional ghost correction," Phys. Stat. Sol. (b) 112 (1982), K111–120) or an modified ADC method (K. Pawlik, Phys. Stat. Sol. (b) 124 (1986), 477).

The pole densities $P^{hkl}(\Psi,\Phi)$ are calculated for each (hkl) orientation of interest and for each $(\Psi,\Phi)$ direction by applying an appropriate projection operator to the ODF. (S. Mathis, G. W. Vinel, K. Helming, Standard Distributions in Texture Analysis (Akademie-Verlag, Berlin, 1987)).

Figure 1:
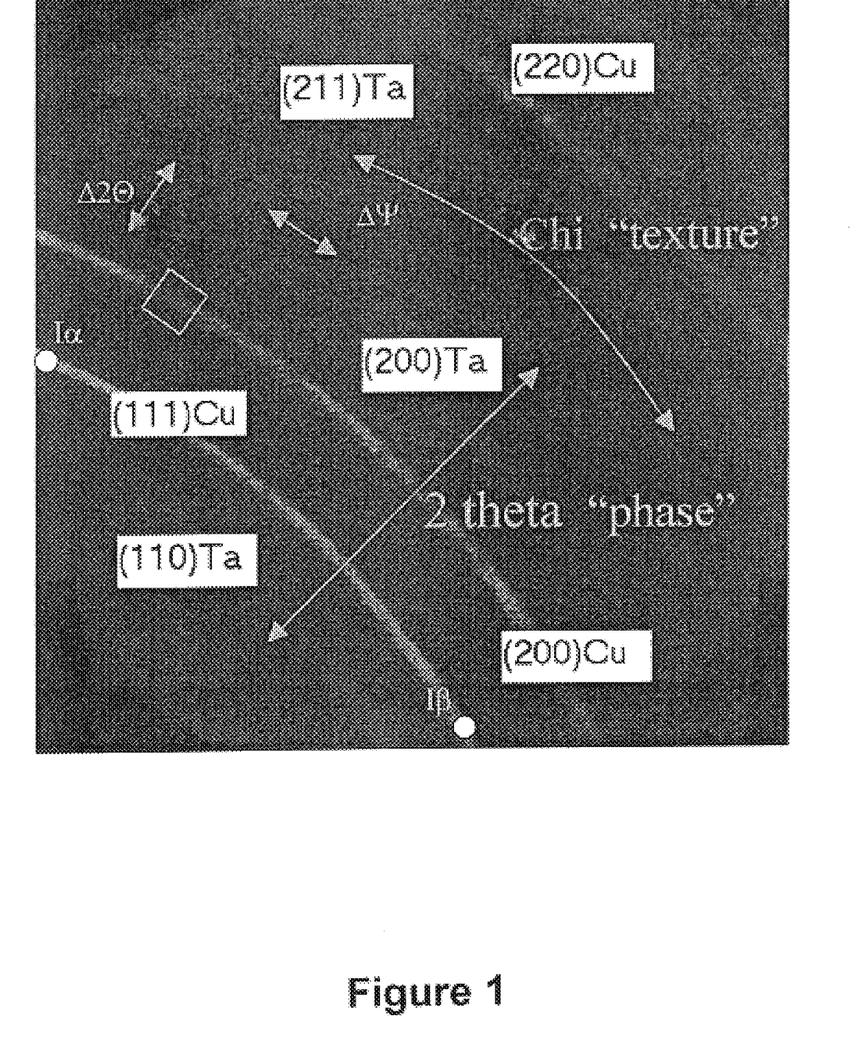
FIG. 1 shows a diffraction frame captured by an area detector.

The values of diffraction intensities for the (hkl) orientation of interest within an integration region i, as finely meshed over small increments of $\Delta\Psi$ and $\Delta 2\theta$ (usually not more than 1 degree), are then obtained from the diffraction image captured by the area x-ray detector, as in FIG. 1. An example of the integration region i is shown by the square on the Debye ring originating from the (200) planes of Cu in FIG. 1. The obtained diffraction intensity as measured within integration region i is $\{I_{textured}^{hkl}(\Psi,\Phi)\}_i$.

The discrete values of $P^{hkl}(\Psi,\Phi)_i$ corresponding to the region i, as calculated from the ODF, are then used to correct the discrete values of the measured diffraction intensities $\{I_{textured}^{hkl}(\Psi,\Phi)\}_i$ according to equation (7), to eliminate the impact of the crystallographic texture from the measured diffraction intensity. Therefore, the discrete values of measured diffraction intensities $\{I_{textured}^{hkl}(\Psi,\Phi)\}_i$ collected on the textured sample are converted to their equivalent random diffraction intensities $\{I_{random}^{hkl}(\Psi,\Phi)\}_i$ as follows:

$$\{I_{random}^{hkl}(\Psi,\Phi)\}_i {}_{i=}\{I_{textured}^{hkl}(\Psi,\Phi)\}_i/P^{hkl}(\Psi,\Phi)_i \qquad (8)$$

By integrating the values of equivalent random diffraction intensities $\{I_{random}^{hkl}(\Psi,\Phi)\}_i$ of the (hkl) reflection, total random diffraction intensity $I_{randomtotal}^{hkl}$ can be obtained, according to the following equation:

$$I_{randomtotal}^{hkl} = \sum_{i=1}^{i=N} I_{random}^{hkl}(\Psi,\Phi)_i / N \qquad (9)$$

$$N=\{(\Psi_{max}-\Psi_{min})/\Delta\Psi\}(2\pi/\Delta\Phi) \qquad (9)$$

wherein the summation is carried out on all locations $(\Psi,\Phi)$ of the experimental pole figure (hkl) collected with the resolution of $\Delta\Psi$ and $\Delta\Phi$ in the radial and azimuthal directions, respectively.

From the corrected and integrated diffraction intensity $I_{randomtotal}^{hkl}$ for each phase, one can readily and accurately calculate the weight or volume fraction of such in a sample mixture, according to equations (2), (3), (4), and (5).

Another method of obtaining corrected and integrated intensity that can be used for quantitative phase analysis in equations (2), (3), (4), and (5) is based upon averaging the registered diffraction intensities $\{I_{textured}^{hkl}(\Psi,\Phi)\}_i$ over all orientations in the pole figure space and then integrating all the averaged diffraction intensities.

Because the pole figures measured are incomplete, part of the diffraction intensities is missing. Therefore, a correction factor c for compensating the missing diffraction intensity is calculated as follows:

$$c = \frac{\sum_{\Psi=0}^{\Psi=\pi/4} \sum_{\Phi=0}^{\Phi=2\pi} P_i^{hkl}(\Psi, \Phi)_{calculated}}{\sum_{\Psi=\Psi_{min}}^{\Psi=\Psi_{max}} \sum_{\Phi=0}^{\Phi=2\pi} P_i^{hkl}(\Psi, \Phi)_{calculated}} \quad (10)$$

where $\Psi_{min}$, and $\Psi_{max}$ are the limits of the measured incomplete pole figure, and the $P_i^{hkl}(\Psi,\Phi)_{calculated}$ are the pole densities re-calculated from the ODF.

The corrected and integrated total diffraction intensity, which is equivalent to that from a perfectly random sample, is calculated as:

$$I_{randomtotal}^{hkl} = c \sum_{\Psi=\Psi_{min}}^{\Psi=\Psi_{max}} \sum_{\Phi=0}^{\Phi=2\pi} \{I_{textured}^{hkl}(\Psi, \Phi)\}_i \quad (11)$$

Alternatively, the corrected and integrated intensity may be obtained by summing all intensities collected on a complete or near-complete (i.e., with a ($Y_{max}-Y_{min}$) range less than couple of degrees) pole figure.

The calculation of pole densities can be simplified if the area detector is sufficiently close to the sample measurement point for capturing a whole Debye cone (e.g., in a transmission mode) or a diffraction arc that covers a $\Psi$ range of not less than 90 degrees for a particular (hkl) phase. A diffraction image with a whole Debye cone (360 degrees) or a diffraction arc of not less than 90 degrees is equivalent to measurement of a full pole figure, and the pole densities $P^{hkl}(\Psi,\Phi)$ can be directly calculated by using a normalization equation (12) as follows, without having to calculate such pole densities from ODF:

$$\frac{1}{4\pi} \int_0^\pi \int_0^{2\pi} P^{hkl}(\Psi, \Phi) \sin\Psi \, d\Psi = 1 \quad (12)$$

Moreover, when the textured polycrystalline materials are in form of thin films or coatings having fiber texture (i.e., each crystallite or grain has the same particular crystallographic orientation parallel to a particular direction on the sample, for example, the direction normal to the sample surface, and is randomly rotated around this axis), the pole density is independent of the azimuthal polar coordinate $\Phi$ and can be expressed as $P^{hkl}(\Psi)$. The fiber symmetry may be experimentally enforced by spinning the sample during measurements. In such a case the measurement protocol is simplified in a sense that the $\Phi$ rotation of the samples are not necessary and only one diffraction frame registered by the area detector is sufficient for quantitative phase analysis.

A further aspect of the present invention relates to a quantitative phase analysis system, comprising:

a sample comprising a mixture of two or more textured polycrystalline materials, such sample defining an associated sample plane;

a radiation source for directing radiation energy to a measurement point on the sample;

a 2-dimensional detector that registers radiation energy diffracted from the sample at the measurement point, with the radiation source and the 2-dimensional detector being in a fixed spatial relationship to one another and sufficiently proximate to the measurement point to capture a plurality of diffraction arcs within a single data capture frame of the area detector;

a sample motion assembly for translating the sample in the sample plane; and a computer-based quantitative phase analyzer, constructed and arranged to collect and process diffraction data for analyzing phase compositions of the sample.

The quantitative phase analysis system of the present invention significantly reduces the data acquisition time required, by employing a collimated source of monochromatic radiation energy, for directing radiation energy to a measurement point on a sample, and a 2-dimensional detector for registering radiation energy diffracted from the measurement point, with the collimated source of radiation energy and the 2-dimensional detector being in a fixed spatial relationship to each other and sufficiently proximate to the sample measuring point to capture a plurality of diffraction arcs within a single data capture frame of the detector.

The use of an area x-ray detector, as opposed to the point scanning detectors traditionally used for detecting diffracted x-ray beams, greatly reduces data acquisition time by capturing a relatively large range of the reciprocal space, and storing it as a digitized electronic file. Multiple diffraction arcs can thus be captured in a single detector frame, both reducing data acquisition time and increasing accuracy.

The x-ray beam source and area x-ray detector of the present invention are arranged in carefully chosen fixed spatial locations, which determine correspondingly fixed ranges of sample coverage in 2θ and Ψdirections. Conventional x-ray diffraction systems require movement of the detector in the 2θ direction and movement of the sample in the Ψ direction in order to obtain a sufficiently complete pole figure for calculating the orientation distribution functions. In contrast, the present invention, by fixing the spatial relationship between the x-ray beam source and area x-ray detector, fixes the sample coverage in 2θ and Ψ directions and thus eliminates motion of the detector and sample in these two directions.

Moreover, such fixed spatial locations between the x-ray beam source and area x-ray detector are optimally integrated with a particular set of sample motions (usually planar motion within the sample plane defined by the sample holding device in order to obtain sufficient texture information), and optimally integrated with a primary set of materials that the inventive system is used to analyze. This enables the elimination of the conventional Eulerian cradle used to rotate the sample in the Ψ direction, the θ rotating stage used to rotate the sample, and the 2θ rotating stage used to rotate the detector, as required in the prior art systems to obtain a sufficiently complete pole figure. Elimination of these motion stages greatly simplifies the system and significantly reduces its cost.

Figure 2:
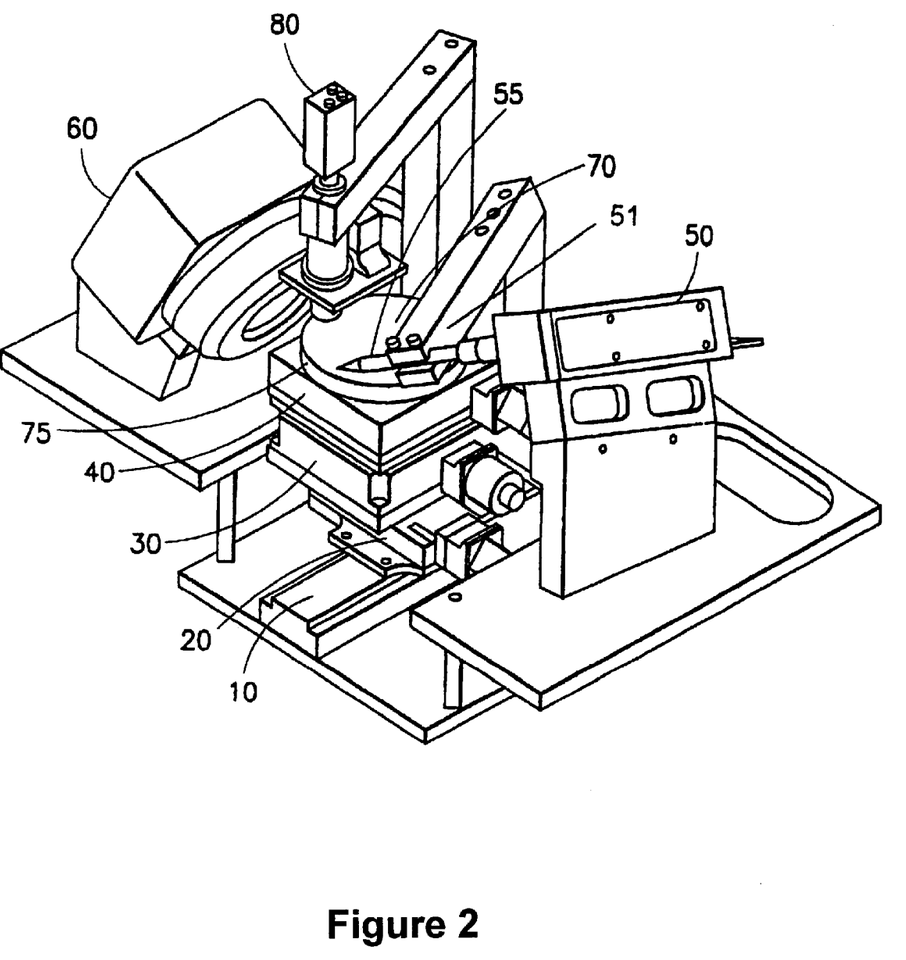
FIG. 2 shows an apparatus used in the present invention.

An example of the apparatus used in the present invention is shown in FIG. 2. The apparatus of the present invention utilizes an x-ray source with collimation device and an area x-ray detector with its positioning optimized for a particular range of coverage within reciprocal space.

The apparatus preferably comprises three interacting components: the collimated x-ray source components, the sample handling apparatus, and the area detector. The x-ray area detector 60 is mounted to a rigid base. Also mounted to the rigid base are the x-ray source 50, monochromator 51, and x-ray collimator 55. In this particular example, the sample handling apparatus consists of a sample motion apparatus, having a y-stage 10, an x-stage 20, a z-stage 30, and a φ-stage 40. Also shown is an optional video microscope 80. The example application of the invention is primarily designed to handle sample 70 up to 300 millimeters in diameter, but the apparatus can be readily modified to handle larger or smaller samples.

A preferred aspect of the invention is that it fixes the x-ray source and detector in specific spatial locations. The sample handling apparatus is mounted in such a way to not spatially interfere with the x-ray source, collimator or detector, but allow sample motion sufficient to cover all locations of the sample surface, and to also allow in-plane rotation at all of these locations. In the example configuration, the sample motion stages are arranged in the following order from top to bottom: φ rotation, z (vertical) motion, x linear motion, and y linear motion. These sample motions are configured in such a way as to allow full sample motion, as well as close proximity of the area detector to the wafer measure point 75.

In the present invention, the fixed ranges of 2θ and Ψ are optimized for a group of specific material systems, by placing the detector 60 and x-ray source 50 at very specific permanent locations. By capturing a desired set of crystallographic reflections over a preferred range of Ψ for each reflection, the maximum amount of texture information can be extracted from the measurement process through a new and more efficient analysis.

A Hi-Star® multiwire gas proportional counter, produced by Bruker AXS, Madison, Wis., is currently a preferred area x-ray detector suitable for diffraction data acquisition in polycrystalline materials. It offers high sensitivity combined with a large total circular detection area that is 11.5 centimeters in diameter. Any other suitable two-dimensional type area detector with sufficient angular range and spatial resolution can be employed, including, but not limited to, x-ray image charge-coupled device (CCD) cameras, x-ray image plates, and other 2-D x-ray detectors. Preferably, such area detector has large area, high sensitivity, and a mechanism for rapid transfer of data to electronic digital format.

The x-ray source can be a standard monochromatic sealed beam tube, a rotating anode, an integrated sealed tube—polycaplilary optics system, an integrated sealed tube—grated mirror system or any other suitable source for generating and collimating x-rays.

Additional information concerning the apparatus arrangement, is contained in U.S. Pat. No. 6,301,330 for "Apparatus and Method for Texture Analysis on Semiconductor Wafers" issued on Oct. 9, 2001, the contents of which are herein incorporated by reference in their entireties for all purposes.

The phase composition of the sample is determined by a computer-based quantitative phase analyzer, which may comprise a computer, central processor unit (CPU), microprocessor, integrated circuitry, operated and arranged to collect and process diffraction data for determining phase composition of textured polycrystalline thin film or any other multiphase sample, according to the method described hereinabove. Such quantitative phase analyzer preferably comprises a phase composition determination protocol for computationally carrying out the phase composition determination method described hereinabove. The phase composition determination protocol can be embodied in any suitable form, such as software operable in a general-purpose programmable digital computer. Alternatively, the protocol may be hard-wired in circuitry of a microelectronic computational module, embodied as firmware, or available on-line as an operational applet at an Internet site for phase analysis.

Although the invention has been variously disclosed herein with reference to illustrative embodiments and features, it will be appreciated that the embodiments and features described hereinabove are not intended to limit the invention, and that other variations, modifications and alternative embodiments will readily suggest themselves to those of ordinary skill in the art. The invention therefore is to be broadly construed, as including such variations, modifications and alternative embodiments, within the spirit and scope of the ensuing claims.

What is claimed is:

1. A method for quantitatively determining phase composition of a sample mixture that comprises textured polycrystalline materials of multiple phases, said method comprising the steps of:
   (a) collecting multiple incomplete pole figures for the multiple phases of said sample mixture, by steps that comprise:
      (i) irradiating a measurement area on the sample mixture with radiation energy from a radiation source;
      (ii) detecting the radiation energy diffracted from the sample mixture at a detection locus, wherein the detection locus is positioned in such a way as to capture a plurality of diffraction arcs within a single data capture frame; and
      (v) generating a diffraction image containing multiple incomplete pole figures for the multiple phases;
   (b) calculating complete pole density distribution for a first set of crystallographic planes (hkl) of a first phase contained by the sample mixture, based on the incomplete pole figures collected on the diffraction image;
   (c) correcting diffraction intensities collected on the diffraction image for the first set of crystallographic planes (hkl) of the first phase to eliminate crystallographic texture therefrom, by using the complete pole density distribution calculated in step (b);
   (d) integrating the corrected values of diffraction intensities for the first set of crystallographic planes (hkl) of the first phase;
   (e) repeating steps (b)–(d) to obtain integrated and corrected diffraction intensities for all phases contained by the sample mixture; and
   (f) calculating the phase composition of the sample mixture from the corrected and integrated diffraction intensities obtained in steps (d) and (e).

2. The method of claim 1, wherein the sample mixture comprises two textured polycrystalline materials of known crystal structures and lattice parameters.

3. The method of claim 1, wherein the sample mixture comprises more than two textured polycrystalline materials of known crystal structures and lattice parameters.

4. The method of claim 1, wherein the phase composition of the sample mixture is calculated from the corrected and integrated diffraction intensities according to a direct comparison method.

5. The method of claim 1, wherein the phase composition of the sample mixture is calculated from the corrected and integrated diffraction intensities according to a standardless method.

6. The method of claim 1, wherein the phase composition of the sample mixture is calculated from the corrected and integrated diffraction intensities according to a standardless mapping method.

7. The method of claim 1, wherein the complete pole density distribution for a set of crystallographic planes (hkl) of a phase in step (b) is calculated by the steps comprising:
   (i) calculating Orientation Distribution Function (ODF) based on the multiple incomplete pole figures collected by step (a); and
   (ii) calculating the complete pole density distribution for the set of crystallographic planes (hkl) of said phase from the Orientation Distribution Function.

8. The method of claim 7, wherein the Orientation Distribution Function in step (i) is calculated by using a direct method with an arbitrary step resolution.

9. The method of claim 8, wherein the direct method is selected from the group consisting of the Williams-Imhof-Matthies-Vinel (WIMV) method and the Arbitrary Defined Cell (ADC) method.

10. The method of claim 8, wherein the arbitrary step is not more than 5 degrees.

11. The method of claim 8, wherein the arbitrary step is not more than 1 degree.

12. The method of claim 1, wherein in step (a)(ii), said detection locus is in sufficient proximity to said measurement area for capturing at least one diffraction arc of not less than 90 degrees, and wherein the complete pole density distribution in step (b) is directly calculated for a particular set of crystallographic planes (hkl) reflected by said at least one diffraction arc, by using a normalization equation.

13. The method of claim 12, wherein said detection locus is in sufficient proximity to said measurement area for capturing at least one diffraction arc of about 360 degrees.

14. The method of claim 1, wherein in step (a)(ii), the detection locus is in fixed spatial relationship to the radiation source.

15. A method for quantitatively determining phase composition of a sample mixture that comprises textured polycrystalline materials of multiple phases, said method comprising the steps of:
   (a) collecting multiple incomplete pole figures for the multiple phases of said sample mixture, by steps that comprise:
      (i) irradiating a measurement area on the sample mixture with radiation energy from a radiation source;
      (ii) detecting the radiation energy diffracted from the sample mixture at a detection locus, wherein the detection locus is positioned in such a way as to capture a plurality of diffraction arcs within a single data capture frame; and
      (vi) generating a diffraction image containing multiple incomplete pole figures for the multiple phases;
   (b) averaging diffraction intensities collected on the diffraction image for a first set of crystallographic planes (hkl) of a first phase over all crystallographic orientations of the incomplete pole figures collected on the diffraction image;
   (c) integrating the averaged values of diffraction intensities for the first set of crystallographic planes (hkl) of the first phase in step (b);
   (d) correcting the integrated diffraction intensities in step (c) with a correction factor, which is the ratio of complete pole density distribution over incomplete pole density distribution measured for the first set of crystallographic planes (hkl) of the first phase;
   (e) repeating steps (b)–(d) to obtain integrated and corrected diffraction intensities for all phases contained by the sample mixture; and
   (f) calculating the phase composition of the sample mixture from the corrected and integrated diffraction intensities obtained in steps (d) and (e).

16. The method of claim 15, wherein the sample mixture comprises two textured polycrystalline materials of known crystal structures and lattice parameters.

17. The method of claim 15, wherein the sample mixture comprises more than two textured polycrystalline materials of known crystal structures and lattice parameters.

18. The method of claim 15, wherein the phase composition of the sample mixture is calculated from the corrected and integrated diffraction intensities according to a direct comparison method.

19. The method of claim 15, wherein the phase composition of the sample mixture is calculated from the corrected and integrated diffraction intensities according to a standardless method.

20. The method of claim 15, wherein the phase composition of the sample mixture is calculated from the corrected and integrated diffraction intensities according to a standardless mapping method.

21. A quantitative phase analysis system for determining phase composition of a sample mixture that comprises textured polycrystalline materials of multiple phases, comprising:
   a sample comprising a mixture of two or more textured polycrystalline materials, said sample defining an associated sample plane;
   a radiation source for directing radiation energy to a measurement point on the sample;
   a 2-dimensional detector that registers radiation energy diffracted from the sample at the measurement point, with the radiation source and the 2-dimensional detector being in a fixed spatial relationship to one another and sufficiently proximate to the measurement point to capture a plurality of diffraction arcs within a single data capture frame of the area detector;
   a sample motion assembly for translating the sample in the sample plane; and
   a computer-based quantitative phase analyzer, constructed and arranged to collect and process diffraction data for analyzing phase compositions of the sample.

* * * * *

UNITED STATES PATENT AND TRADEMARK OFFICE
CERTIFICATE OF CORRECTION

PATENT NO. : 6,678,347 B1
DATED : January 13, 2004
INVENTOR(S) : Kozaczek et al.

It is certified that error appears in the above-identified patent and that said Letters Patent is hereby corrected as shown below:

Column 1,
Line 35, "Modem" should be -- Modern --

Column 4,
Line 59, in equation (1): "with 1 $i$ $n$, and 1 $j$ $n$" should be -- with $1<i<n$ and $1<j<n$ --

Column 5,
Line 10 in equation (2): "with 1 $i$ $n$, and 1 $j$ $n$" should be -- with $1<i<n$, and $1<j<n$ --
Line 47, "$c_{i+1}$ and $c_{i+1}$" should be -- $c_i$ and $c_{i+1}$ --
Line 49, "$R_{i-1}$" should be -- $R_{i+1}$ --

Column 7,
Line 41, "materials. (II)" should be -- materials.: (III) --

Signed and Sealed this

Twenty-seventh Day of July, 2004

JON W. DUDAS
*Acting Director of the United States Patent and Trademark Office*